(12) United States Patent
Park et al.

(10) Patent No.: US 11,096,906 B2
(45) Date of Patent: Aug. 24, 2021

(54) PHARMACEUTICAL COMPOSITION FOR PREVENTING OR TREATING ALZHEIMER'S DISEASE

(71) Applicant: SFCBIO. CO., LTD., Seoul (KR)

(72) Inventors: So-Young Park, Cheonan-si (KR); Hwan-Bin Joo, Cheonan-si (KR)

(73) Assignee: SFCBIO. CO., LTD., Seoul (KR)

( * ) Notice: Subject to any disclaimer, the term of this patent is extended or adjusted under 35 U.S.C. 154(b) by 12 days.

(21) Appl. No.: 15/777,529

(22) PCT Filed: Nov. 18, 2016

(86) PCT No.: PCT/KR2016/013351
§ 371 (c)(1),
(2) Date: May 18, 2018

(87) PCT Pub. No.: WO2017/086743
PCT Pub. Date: May 26, 2017

(65) Prior Publication Data
US 2018/0325841 A1 Nov. 15, 2018

(30) Foreign Application Priority Data

Nov. 18, 2015 (KR) .................. 10-2015-0161805

(51) Int. Cl.

| | | |
|---|---|---|
| *A61K 31/12* | (2006.01) | |
| *A61K 36/11* | (2006.01) | |
| *A61K 31/473* | (2006.01) | |
| *A61K 31/445* | (2006.01) | |
| *A61K 31/27* | (2006.01) | |
| *A61K 31/55* | (2006.01) | |
| *A61K 36/12* | (2006.01) | |
| *A61P 25/28* | (2006.01) | |

(52) U.S. Cl.
CPC .............. *A61K 31/12* (2013.01); *A61K 31/27* (2013.01); *A61K 31/445* (2013.01); *A61K 31/473* (2013.01); *A61K 31/55* (2013.01); *A61K 36/11* (2013.01); *A61K 36/12* (2013.01); *A61P 25/28* (2018.01)

(58) Field of Classification Search
CPC ...... A61K 31/12; A61K 31/27; A61K 31/445; A61K 31/473; A61K 31/55; A61K 36/11; A61K 36/12; A61P 25/28
See application file for complete search history.

(56) References Cited

U.S. PATENT DOCUMENTS

2017/0320802 A1\* 11/2017 Bharate ................ C07D 311/96

FOREIGN PATENT DOCUMENTS

| KR | 10-2010-0012927 A | 2/2010 | |
|---|---|---|---|
| KR | 10-2010-0082090 A | 7/2010 | |
| KR | 10-2011-0035570 A | 4/2011 | |
| KR | 10-2013-0028261 A | 3/2013 | |
| KR | 10-2013-0138940 A | 12/2013 | |
| KR | 101461591 B1 \* | 11/2014 | ........... A61K 31/045 |

OTHER PUBLICATIONS

English Translation KR 1020130028261 A Published Mar. 19, 2013 (Year: 2013).\*
EnglishTranslation of KR 101461591A Published Nov. 19, 2014 (Year: 2014).\*
Li et al. Laboratory Investigation Apr. 1998 vol. 78 No. 4, pp. 461-469 (Year: 1998).\*
Yang E-J et al. (2015) Phloroglucinol Attenuates the Cognitive Deficits of the 5XFAD Mouse Model of Alzheimer's Disease. PLoS ONE 10(8): e0135686. doi:10.1371/journal.pone.0135686 (Year: 2015).\*
Kim, Jae-Moon, et al. "Anti-Amyloidogenic Properties of Dryopteris Crassirhizoma Roots in Alzheimer's Disease Cellular Model." Journal of Food Biochemistry, May 2015, vol. 39., No. 4, pp. 478-484.
Yang, Eun-Jeong, et al. "Phloroglucinol attenuates the cognitive deficits of the 5XFAD mouse model of alzheimer's disease." Plos one, Aug. 2015, pp. 1-20, vol. 10., No. 8, pp. 1-20.
International Search Report dated Feb. 24, 2017, in International Application No. PCT/KR2016/013351.

\* cited by examiner

*Primary Examiner* — Kortney L. Klinkel
*Assistant Examiner* — William Y Lee
(74) *Attorney, Agent, or Firm* — NSIP Law (57) ABSTRACT

The present disclosure relates to a use of a phloroglucinol-based compound and its salt for preventing and treating Alzheimer's disease. The pharmaceutical composition for preventing or treating Alzheimer's disease of the present disclosure fundamentally suppresses the cause of β-amyloid formation, thereby exerting a remarkable effect of allowing ultimate treatment of Alzheimer's disease. The present disclosure provides the use of the single substance, which has been isolated from *Dryopteris crassirhizoma* and identified, for preventing or treating Alzheimer's disease for the first time.

18 Claims, 14 Drawing Sheets

PHARMACEUTICAL COMPOSITION FOR PREVENTING OR TREATING ALZHEIMER'S DISEASE

CROSS REFERENCE TO RELATED APPLICATION(S)

This application is a U.S. National Stage Application of International Application No. PCT/KR2016/013351, filed on Nov. 18, 2016, which claims the benefit under 35 USC 119(a) and 365(b) of Korean Patent Application No. 10-2015-0161805, filed on Nov. 18, 2015, in the Korean Intellectual Property Office.

BACKGROUND

1. Field of the Invention

The present disclosure relates to a use of a phloroglucinol-based compound and its salt for preventing and treating Alzheimer's disease.

2. Description of Related Art

Dementia is a pathological condition which should be distinguished from normal aging. It is divided into Alzheimer's disease, vascular dementia and other dementias caused by alcoholism, trauma and sequela of Parkinson's disease according to the cause. Among them, Alzheimer's disease is known to be caused primarily by the toxicity of the neurotoxic protein β-amyloid.

According to the generally accepted hypothesis, neuronal cell death is induced by β-amyloid through the following process. First, β-amyloid is produced gradually from the amyloid precursor protein (APP) via the amyloidogenic pathway. The produced monomeric β-amyloid is aggregated with each other to form an oligomer. The aggregated form of β-amyloid induces neuronal cell death.

Accordingly, in order to suppress neuronal cell death caused by β-amyloid, it is necessary to suppress the production of the β-amyloid, suppress the aggregation of the monomeric β-amyloid to the oligomer or protect the cells from the toxicity of the β-amyloid.

Currently, acetylcholine precursors or drugs inhibiting the degradation of acetylcholine are administered as dementia medications in order to increase the concentration of acetylcholine in the brain. Representative drugs include tacrine, donepezil, rivastigmine, galantamine, etc.

Because the existing dementia medications mainly inhibit the acetylcholinesterase without preventing the formation or aggregation of β-amyloid, they cannot ultimately prevent or cure dementia. In addition, because the existing dementia medications are cholinergic drugs, they have the problems that they cannot be administered in combination with other cholinergic drugs, they may inhibit the effect of anticholinergic drugs, they may stimulate the vagus nerve by acting on the cardiovascular system and care should be taken when they are used in patients with a history of severe asthma or obstructive pulmonary disease.

Accordingly, it is the utmost importance to find a method allowing the ultimate treatment of Alzheimer's disease unlike the existing therapeutic agents, i.e., a drug that can suppress the production of β-amyloid while having low toxicity.

The inventors of the present disclosure have studied *Dryopteris crassirhizoma* for treatment and prevention of Alzheimer's disease. In doing so, they have found a use of an active ingredient capable of suppressing the production of β-amyloid from the ingredients of the herb, which has never been mentioned or studied regarding Alzheimer's disease, and have completed the present disclosure.

REFERENCES OF RELATED ART

Korean Patent Publication No. 10-2010-0082090.
Korean Patent Publication No. 10-2010-0012927.

SUMMARY OF THE INVENTION

The present disclosure is directed to providing a pharmaceutical composition for preventing or treating Alzheimer's disease.

The present disclosure is also directed to providing a method for preparing a pharmaceutical composition for preventing or treating Alzheimer's disease, which includes extracting and separating an active ingredient from *Dryopteris crassirhizoma* and formulating the same.

The present disclosure provides a pharmaceutical composition for preventing or treating Alzheimer's disease, which contains a phloroglucinol-based compound, an isomer thereof or a salt thereof.

The present disclosure also provides a method for preparing a pharmaceutical composition for preventing or treating Alzheimer's disease, which includes extracting and separating an active ingredient from *Dryopteris crassirhizoma* and formulating the same.

A pharmaceutical composition for preventing or treating Alzheimer's disease of the present disclosure fundamentally suppresses the cause of β-amyloid formation, thereby exerting a remarkable effect of allowing ultimate treatment of Alzheimer's disease.

The present disclosure provides a use of a single substance, which has been isolated from *Dryopteris crassirhizoma* and identified, for preventing or treating Alzheimer's disease for the first time.

DETAILED DESCRIPTION OF THE INVENTION

Hereinafter, the present disclosure is described in more detail.

The present disclosure relates to a pharmaceutical composition for preventing or treating Alzheimer's disease, which contains a phloroglucinol-based compound, an isomer thereof or a salt thereof.

The phloroglucinol-based compound defined in the present disclosure has a basic structure of Chemical Formula 1:

<Chemical Formula 1>

In Chemical Formula 1, the positions 2 and 4 may be substituted with an alkyl or acyl group.

Specifically, the phloroglucinol-based compound of the present disclosure may be one or more selected from a group consisting of butyrylphloroglucinol, 2-propionyl-4-methylphloroglucinol and 2-butyryl-4-methylphloroglucinol.

In an exemplary embodiment of the present disclosure, butyrylphloroglucinol, 2-propionyl-4-methylphloroglucinol and 2-butyryl-4-methylphloroglucinol exert a remarkable effect of inhibiting β-amyloid formation without showing cytotoxicity at an effective concentration (see FIGS. 12-21).

In particular, Compound 3, which showed toxicity at a concentration of 100 μg/mL, reduced the amount of sAPPβ almost perfectly at 20 μg/mL where no toxicity was observed and also effectively decreased the amount of β-secretase in Test Example 1. Considering that an increased administration dose of an active ingredient, etc. generally leads to increased cytotoxicity and drug-related side effects, the remarkable effect at a low administration dose means a high value as a drug for treating Alzheimer's disease.

The pharmaceutical composition of the present disclosure may contain one or more active ingredient selected from a group consisting of butyrylphloroglucinol, 2-propionyl-4-methylphloroglucinol, 2-butyryl-4-methylphloroglucinol, an isomer thereof or a salt thereof.

The pharmaceutical composition of the present disclosure may exert an effect of preventing or treating Alzheimer's disease even when it contains one of butyryiphloroglucinol, 2-propionyl-4-methylphloroglucinol, 2-butyryl-4-methylphloroglucinol, an isomer thereof or a salt thereof as a single active ingredient.

Specifically, the pharmaceutical composition of the present disclosure may exert an effect of preventing or treating Alzheimer's disease even when it contains butyryiphloroglucinol, an isomer thereof or a salt thereof as a single active ingredient.

Also, the pharmaceutical composition of the present disclosure may exert an effect of preventing or treating Alzheimer's disease even when it contains 2-propionyl-4-methylphloroglucinol, an isomer thereof or a salt thereof as a single active ingredient.

In addition, the pharmaceutical composition of the present disclosure may exert an effect of preventing or treating Alzheimer's disease even when it contains 2-butyryl-4-methylphloroglucinol, an isomer thereof or a salt thereof as a single active ingredient.

The salt contained in the pharmaceutical composition of the present disclosure may be a physiologically acceptable salt of an inorganic acid, an organic acid, an inorganic base or an organic base.

For example, the inorganic acid may be hydrochloric acid, bromic acid, sulfuric acid or phosphoric acid, the organic acid may be citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, galacturonic acid, embonic acid, glutamic acid, aspartic acid, etc., although not being limited thereto.

The term Alzheimer's disease used in the present disclosure refers to dementia caused by Alzheimer's disease, i.e., dementia caused by formation and buildup of β-amyloid in the brain tissue. Any dementia caused by formation and buildup of β-amyloid is included in the scope of the present disclosure.

The pharmaceutical composition for preventing or treating Alzheimer's disease containing the phloroglucinol-based compound according to the present disclosure may be applied to an animal including human.

The phloroglucinol-based compound contained in the pharmaceutical composition of the present disclosure may be prepared through chemical synthesis or may be obtained by extracting from *Dryopteris crassirhizoma*.

In an exemplary embodiment of the present disclosure, the phloroglucinol-based compound contained in the pharmaceutical composition of the present disclosure is isolated from *Dryopteris crassirhizoma*. *Dryopteris crassirhizoma* is a perennial grass belonging to the family Dryopteridaceae (Aspidiaceae).

When the phloroglucinol-based compound contained in the pharmaceutical composition of the present disclosure is obtained by extraction, it may be obtained by cold extraction, hot extraction, thermal extraction, ultrasonic extraction, etc. using a commonly used extractor, ultrasonic extractor or fractionator.

The phloroglucinol-based compound contained in the pharmaceutical composition of the present disclosure may be isolated by extracting with one or more solvent selected from a group consisting of propanol, isopropanol and methanol. Specifically, one or more solvent selected from a group consisting of isopropanol or butanol may be used.

Specifically, the solvent used in the extraction may be diluted to 50-99% (v/v) with water.

After extracting *Dryopteris crassirhizoma* with one or more solvent selected from a group consisting of propanol, isopropanol and methanol, removing the remnant of *Dryopteris crassirhizoma* and filtering with filter paper, the filtrate may be concentrated using a vacuum rotary evaporator or a vacuum drier and then stored at room temperature.

The extract may be further fractionated simultaneously or sequentially using one or more solvent selected from a group consisting of hexane, methylene chloride, ethyl acetate, butanol and water. The fractionation solvent may be specifically butanol, more specifically 30-99% (v/v) butanol diluted with water.

The fraction may be concentrated using a vacuum rotary evaporator or a vacuum drier and then stored at room temperature.

The fraction obtained by fractionating simultaneously or sequentially using one or more solvent selected from a group consisting of hexane, methylene chloride, ethyl acetate, butanol and water may be separated by ion-exchange chromatography, silica gel chromatography or medium pressure liquid chromatography (MPLC).

As a solvent used in the chromatography, specifically methanol, acetonitrile or methyl chloride may be used, although not being limited thereto.

The phloroglucinol-based compound according to the present disclosure provides a remarkable use in preventing or treating Alzheimer's disease.

Figure 1:
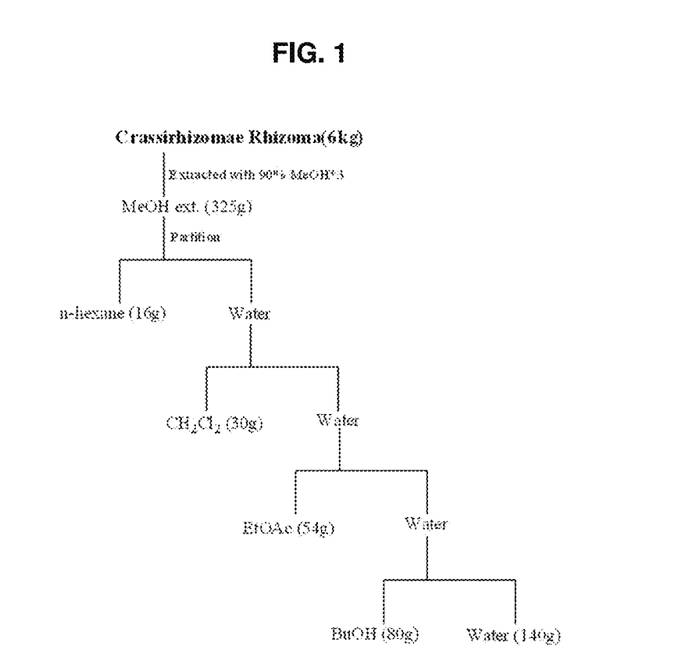
FIG. 1 shows an exemplary extraction process for obtaining a compound according to the present disclosure.
Figure 2:
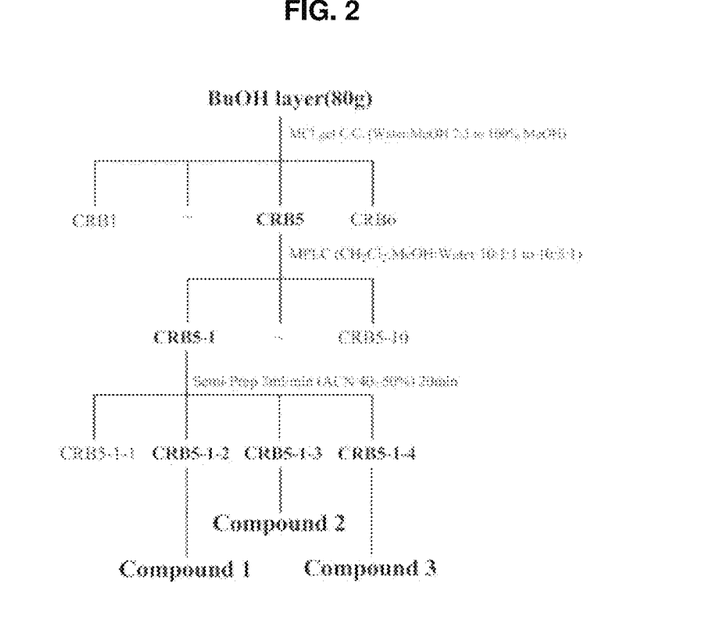
FIG. 2 shows an exemplary process of obtaining fractions for obtaining a compound according to the present disclosure.
Figure 3:
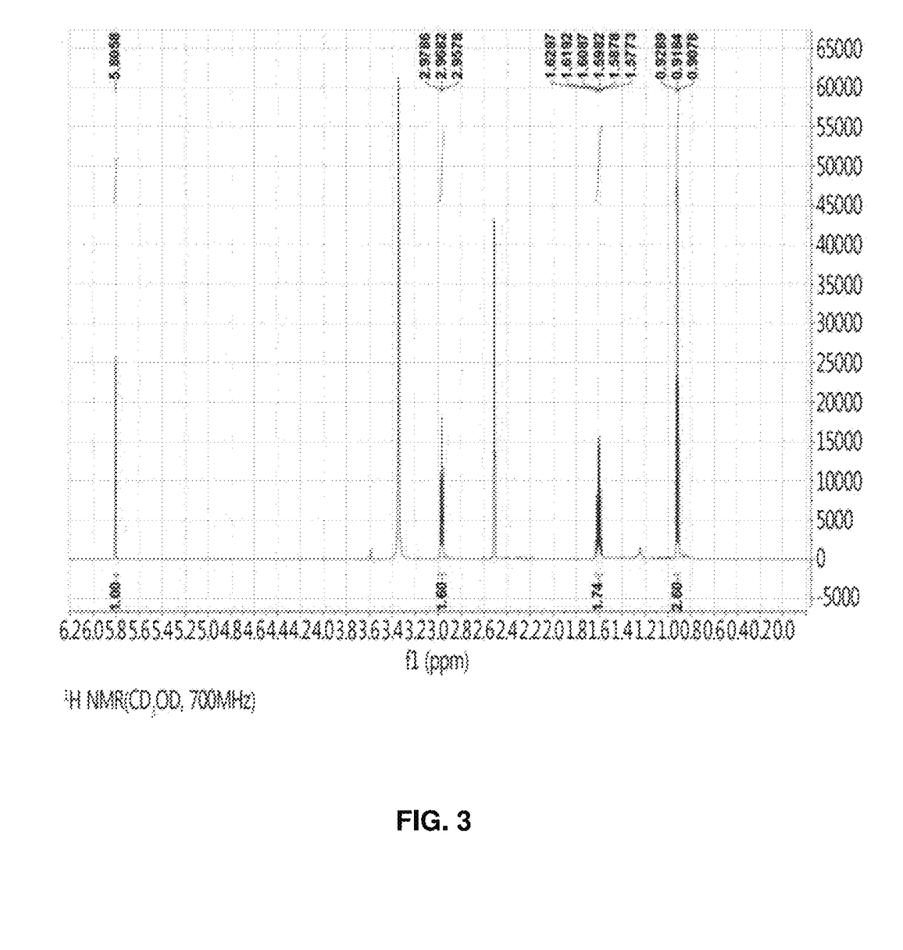
FIG. 3 shows the $^1$H-NMR spectrum of Compound 1 identified as a single substance.
Figure 4:
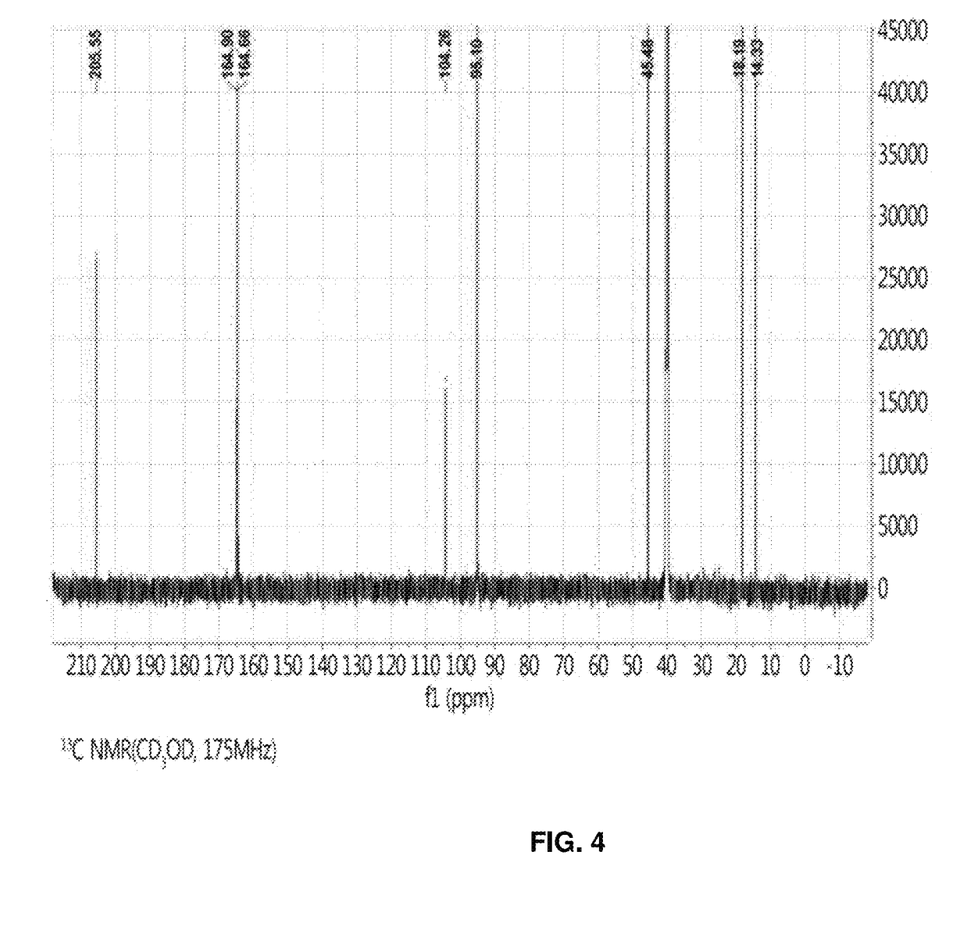
FIG. 4 shows the $^{13}$C-NMR spectrum of Compound 1 identified as a single substance.
Figure 5:
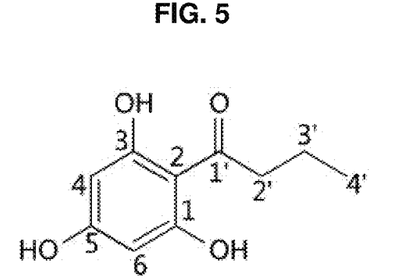
FIG. 5 shows the structure of Compound 1.
Figure 6:
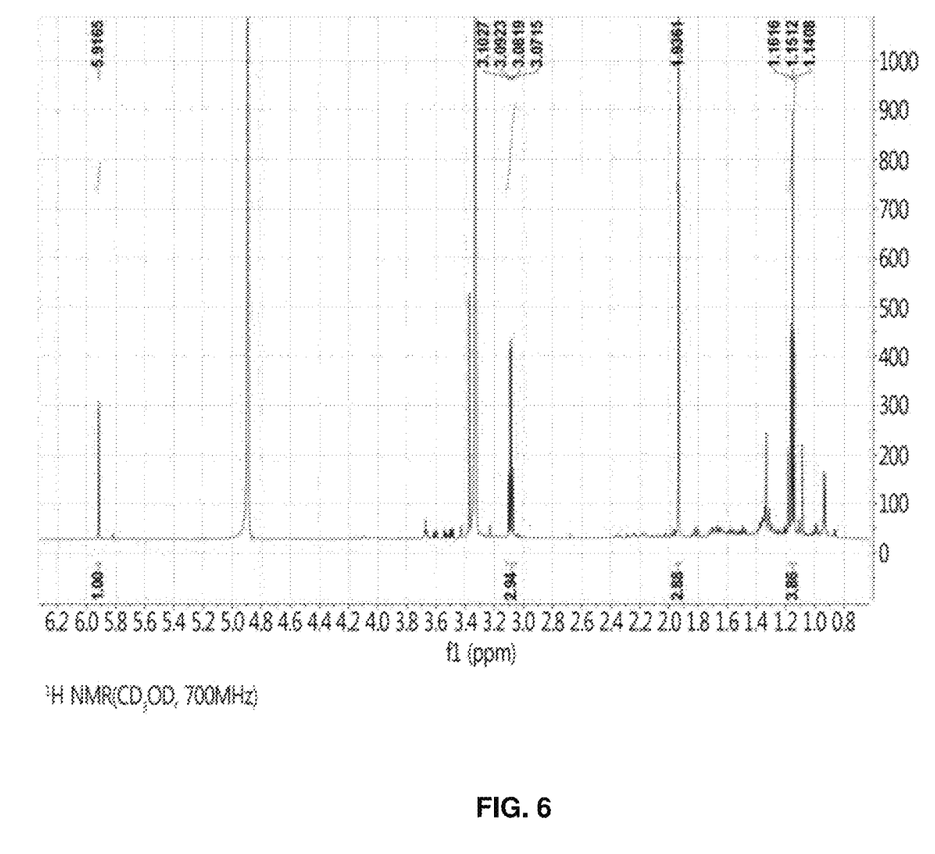
FIG. 6 shows the $^1$H-NMR spectrum of Compound 2 identified as a single substance.
Figure 7:
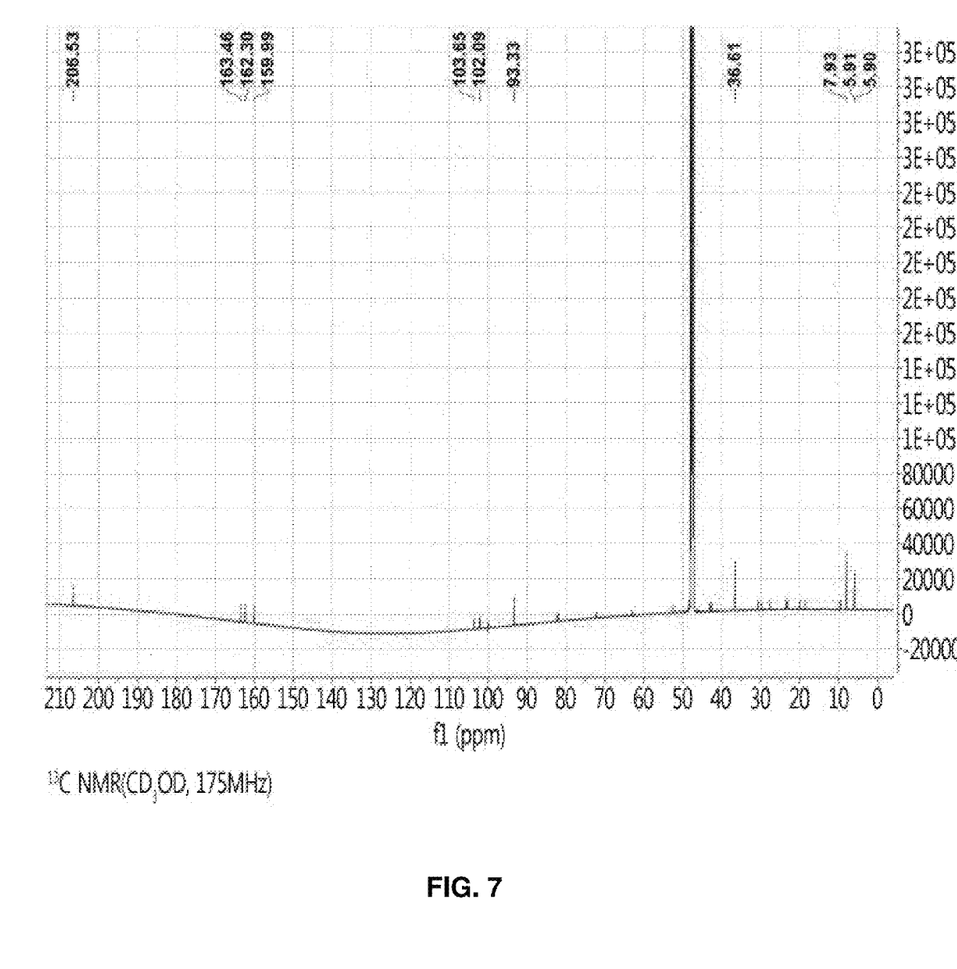
FIG. 7 shows the $^{13}$C-NMR spectrum of Compound 2 identified as a single substance.
Figure 8:
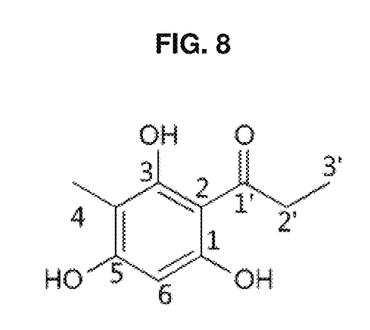
FIG. 8 shows the structure of Compound 2.
Figure 9:
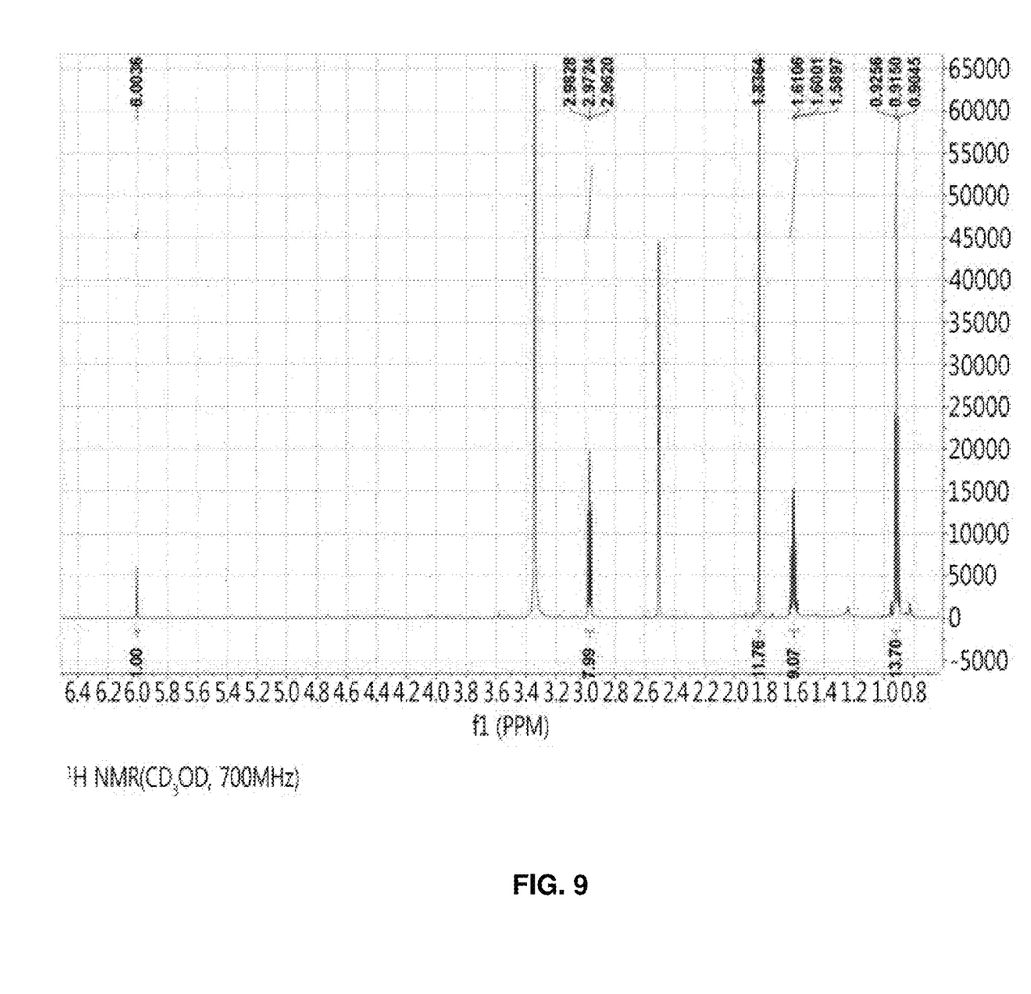
FIG. 9 shows the $^1$H-NMR spectrum of Compound 3 according to the present disclosure.
Figure 10:
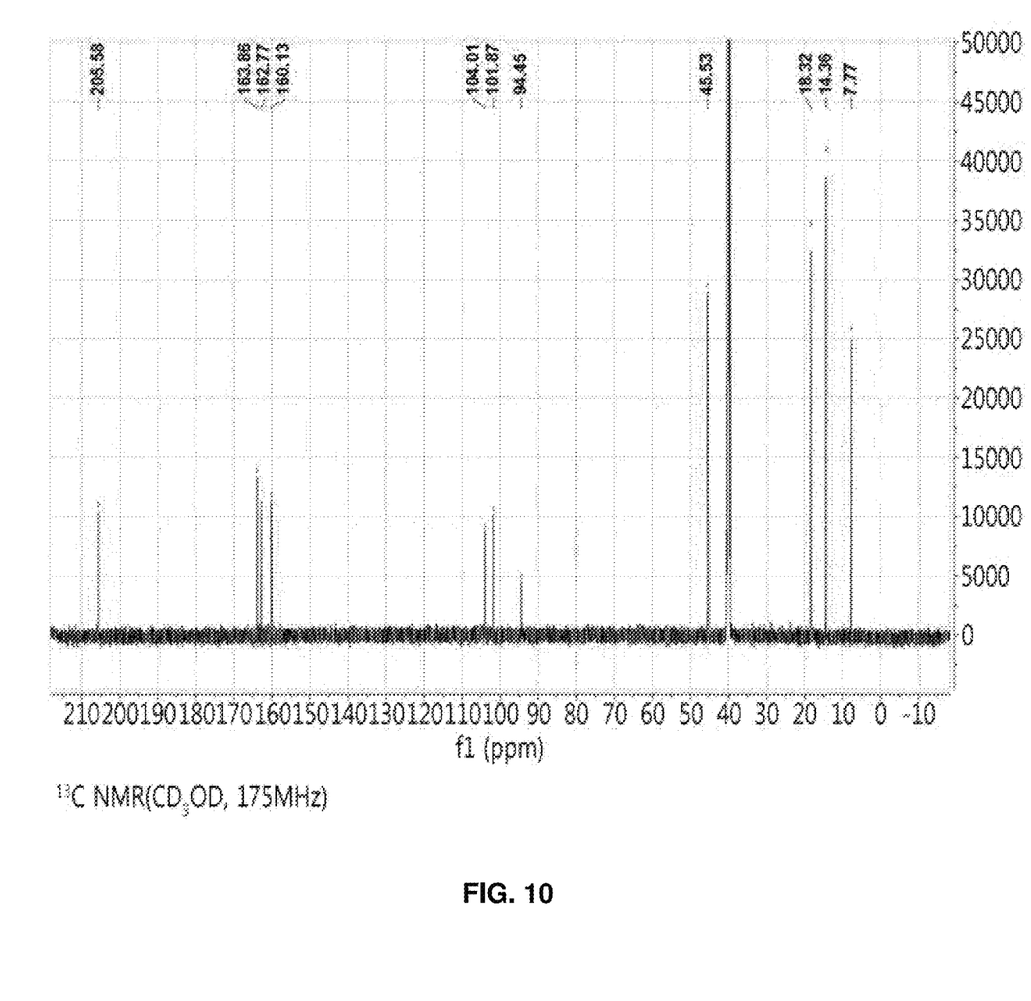
FIG. 10 shows the $^{13}$C-NMR spectrum of Compound 3 according to the present disclosure.
Figure 11:
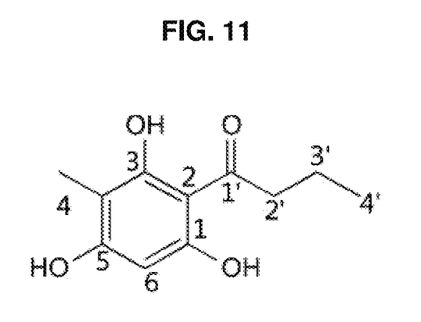
FIG. 11 shows the structure of Compound 3 according to the present disclosure.
Figure 12:
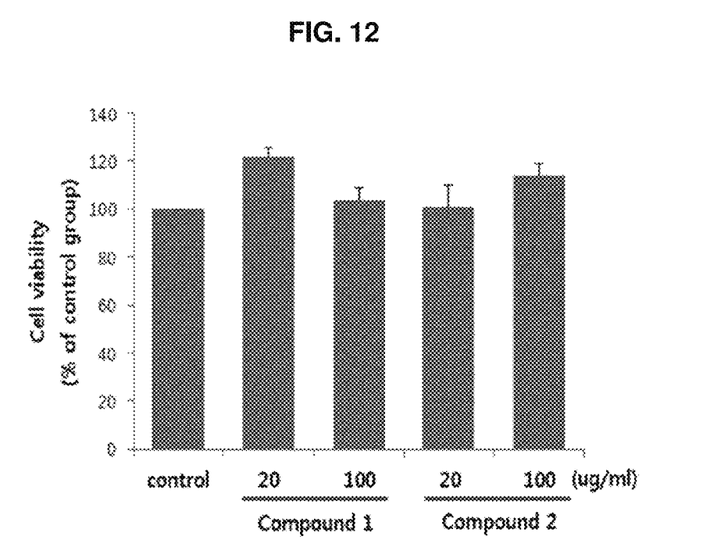
FIG. 12 shows a result of investigating the cytotoxicity of Compounds 1 and 2.
Figure 13:
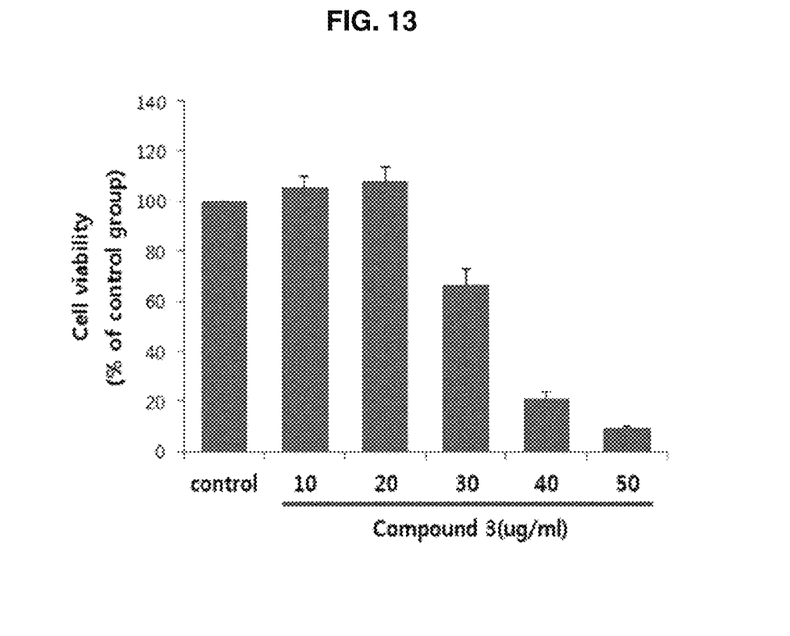
FIG. 13 shows a result of investigating the cytotoxicity of Compound 3.
Figure 14:
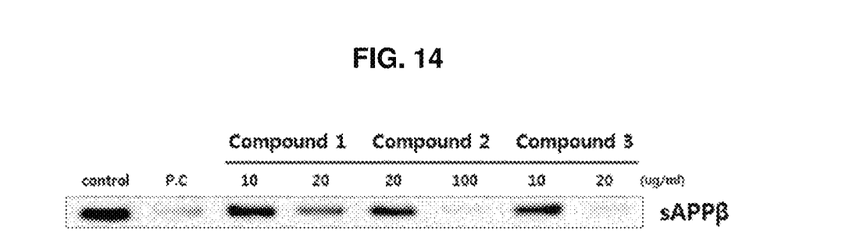
FIG. 14 shows a result of investigating the inhibition of β-amyloid formation by Compounds 1-3 through western blot.
Figure 15:
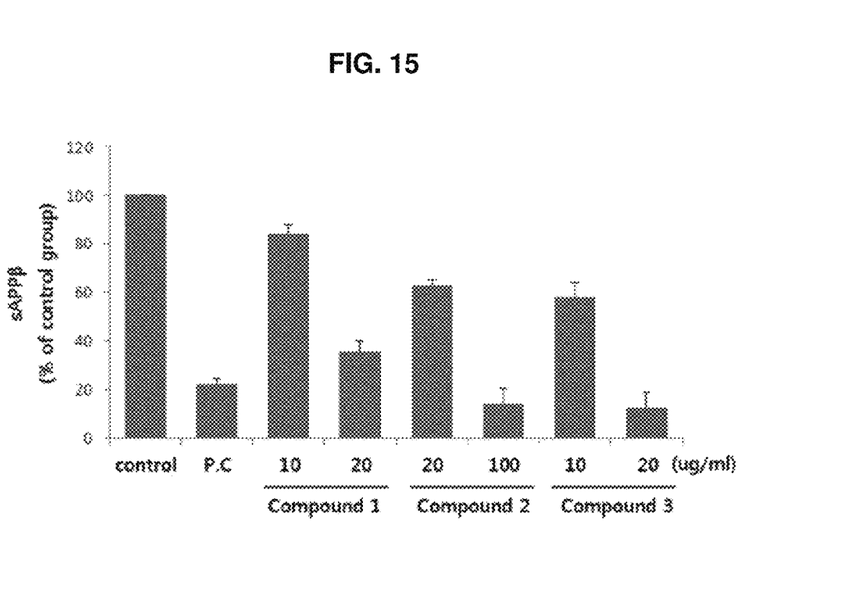
FIG. 15 shows a result of comparing the inhibition of β-amyloid formation by Compounds 1-3.
Figure 16:
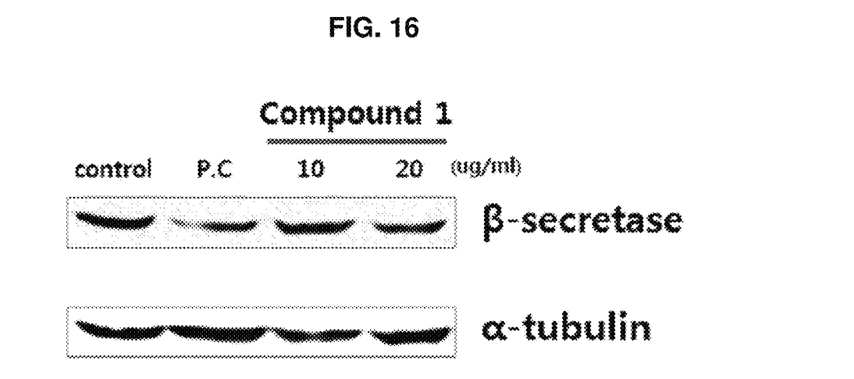
FIG. 16 shows a result of investigating the effect of Compound 1 on β-secretase through western blot.
Figure 17:
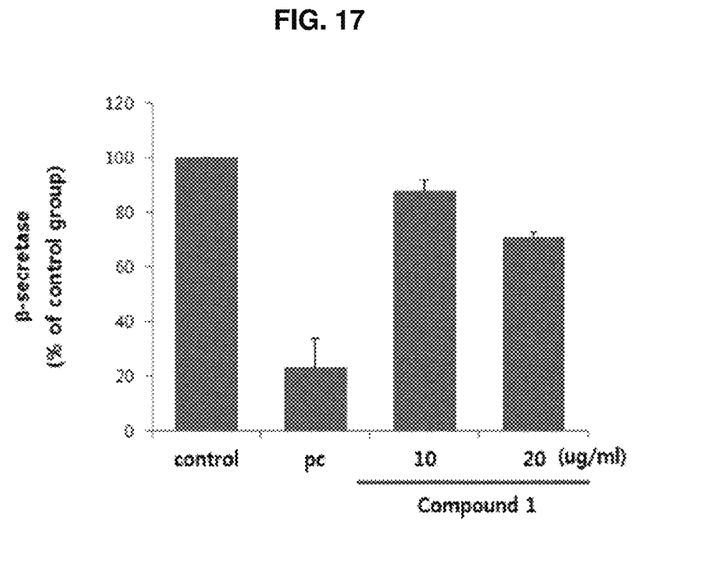
FIG. 17 shows a result of investigating the effect of Compound 1 on β-secretase.
Figure 18:
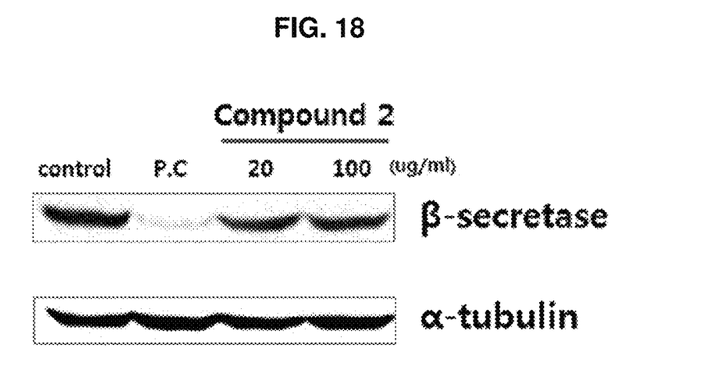
FIG. 18 shows a result of investigating the effect of Compound 2 on β-secretase through western blot.
Figure 19:
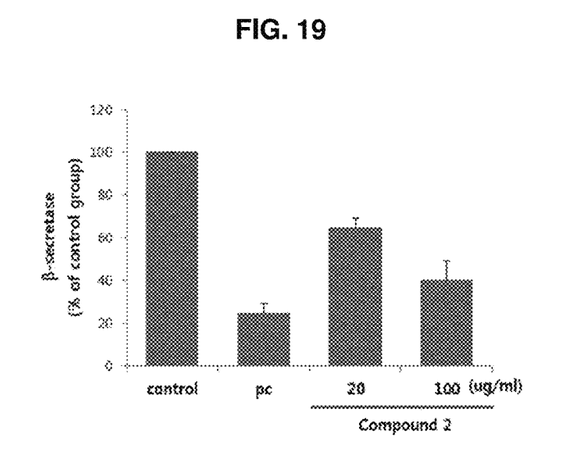
FIG. 19 shows a result of investigating the effect of Compound 2 on β-secretase.
Figure 20:
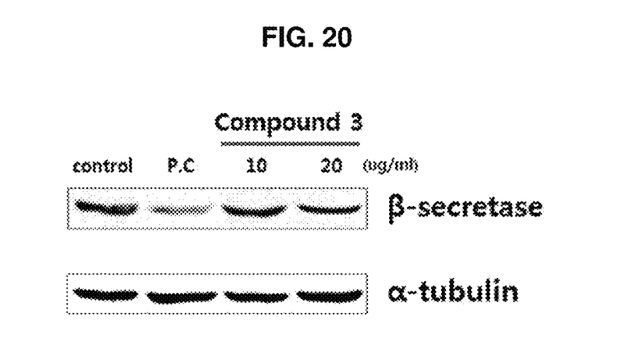
FIG. 20 shows a result of investigating the effect of Compound 3 on β-secretase through western blot.
Figure 21:
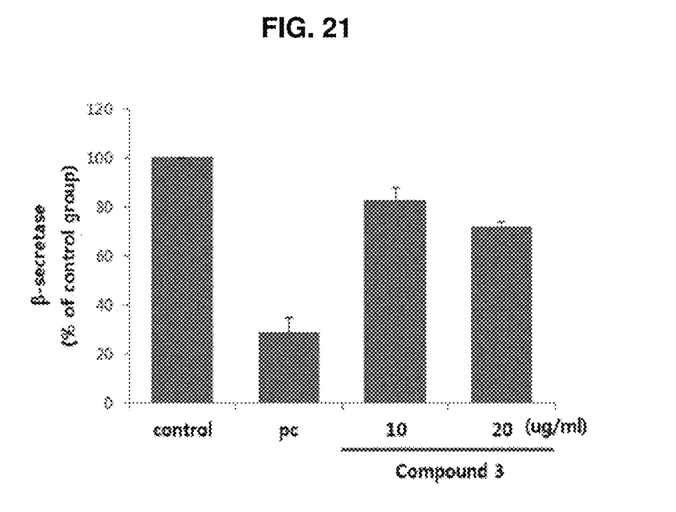
FIG. 21 shows a result of investigating the effect of Compound 3 on β-secretase.

In an exemplary embodiment of the present disclosure, the phloroglucinol-based compound can fundamentally suppress the formation of β-amyloid by reducing sAPPβ in a concentration-dependent manner (see FIGS. 14 and 15).

Also, in an exemplary embodiment of the present disclosure, the phloroglucinol-based compound can fundamentally suppress the formation of β-amyloid by inhibiting β-secretase in a concentration-dependent manner (see FIGS. 16-21).

That is to say, the pharmaceutical composition containing the phloroglucinol-based compound of the present disclosure, an isomer thereof or a salt thereof can suppress the formation of β-amyloid, which is the fundamental problem of Alzheimer's disease, unlike the currently commercially available drugs that simply suppress the progress of Alzheimer's disease through metabolism of acetylcholine, such as tacrine, donepezil, rivastigmine, galantamine, etc. Accordingly, the pharmaceutical composition of the present disclosure can be used directly for preventing and treating Alzheimer's disease.

The administration dose of the pharmaceutical composition according to the present disclosure may be determined by considering administration method, the age, sex and condition of a patient, the severity of a disease, the absorption rate of the active ingredient in vivo, the rate of inactivation and the drug administered in combination. The daily dosage of the active ingredient may be 0.1-500 mg/kg (body weight), specifically 0.1-400 mg/kg (body weight), more specifically 1-300 mg/kg (body weight) and the administration may be made once or several times a day, although not being limited thereto.

The pharmaceutical composition according to the present disclosure may be formulated by containing an inert carrier, a diluent or both of them.

Examples of the inert carrier or diluent may include lactose, dextrose, sucrose, sorbitol, mannitol, xylitol, erythritol, maltitol, starch, corn starch, gum acacia, alginate, gelatin, calcium phosphate, calcium silicate, cellulose, methyl cellulose, microcrystalline cellulose, polyvinylpyrrolidone, citric acid, tartaric acid, water, methyl hydroxybenzoate, propyl hydroxybenzoate, talc, magnesium stearate, mineral oil, dextrin, calcium carbonate, propylene glycol, liquid paraffin, physiological saline, etc., although not being limited thereto.

The pharmaceutical composition of the present disclosure may further contain a commonly used filler, extender, binder, disintegrant, anti-agglomerant, lubricant, wetting agent, pH control agent, nutrient, vitamin, electrolyte, alginic acid or its salt, pectic acid or its salt, protective colloid, glycerin, fragrance, emulsifier, antiseptic, etc. Other suitable lubricants and excipients that may be used are described in the following literatures: Handbook of Pharmaceutical Excipients, 7th edition, American Pharmaceutical Association; The Theory and Practice of Industrial Pharmacy, 3rd edition, Lachman, Leon, 1976; Pharmaceutical Dosage Forms: Tablets Volume 1, 3rd edition, Lieberman, Hebert A., et al., 1989; Modern Pharmaceutics, Banker, Gilbert and Rhodes, Christopher T, 1979; and Remington's Pharmaceutical Sciences, 15th edition, 1975.

The pharmaceutical composition according to the present disclosure may be prepared into an oral or parenteral formulation by containing an additive including the above-described carrier or diluent.

Formulations for oral administration include a tablet, a capsule, a pill, a powder, a granule, a suspension, a syrup, etc. Formulations for parenteral administration include a cream, a lotion, an ointment, a liquid, a gel, a cataplasma, a patch, an aerosol, a fluid extract, an elixir, an infusion, a sachet, an injection, etc.

The content of the phloroglucinol-based compound in the pharmaceutical composition for preventing or treating Alzheimer's disease may be 0.001-99.9 wt %, 0.1-99 wt % or 1-50 wt %. However, the content may be controlled adequately without being limited thereto.

The pharmaceutical composition for preventing or treating Alzheimer's disease of the present disclosure may further contain a substance known to be effective in treating dementia in addition to the active ingredient. Examples may include tacrine, donepezil, rivastigmine, galantamine, etc., although not being limited thereto.

Hereinafter, the present disclosure will be described in detail through examples. However, the following examples are for illustrative purposes only and it will be apparent to those of ordinary skill in the art that the scope of the present disclosure is not limited by the examples.

Example 1: Preparation of *Dryopteris crassirhizoma* Extract or Fractions

1. Preparation of Methanol or Isopropanol Extract of *Dryopteris Crassirhizoma*

After adding 90% methanol to 6 kg of *Dryopteris crassirhizoma* with impurities removed and keeping at room temperature for 24 hours, a filtrate obtained by filtering through filter paper was concentrated using a vacuum rotary evaporator (EYELA). 325 g of an extract in the form of a brown crystalline powder was obtained by repeating this process 3 times. Also, after adding 90% isopropanol to 6 kg of *Dryopteris crassirhizoma* with impurities removed, 390 g of an extract in the form of a brown crystalline powder was obtained through the same procedure.

2. Preparation of Fractions of *Dryopteris crassirhizoma*

The concentrated methanol or isopropanol extract of *Dryopteris crassirhizoma* was fractionated with two immiscible solvents based on the difference in polarity. Hexane, methylene chloride, ethyl acetate, butanol and water layers were fractionated and concentrated sequentially. This process was repeated 3 times. The concentrates were stored at 4° C. until use. 16 g of a hexane layer, 3 g of a methylene chloride layer, 54 g of an ethyl acetate layer, 80 g of a butanol layer and 140 g of a water layer were obtained.

Example 2: Separation and Purification of Compounds 1-3

The fractionated butanol layer extract (80 g) was subjected to MCI column chromatography. 30-100% methanol was used as a mobile phase and a total of 6 fractions were obtained (S1-S6). Based on TLC and HPLC results, the fifth fraction (S5, 3.5 g) was separated by MPLC. The mobile phase started from methylene chloride (MC):MeOH:water (10:1:1) to MC:MeOH:water=10:2:1, 10:3:1, 10:4:1, 10:5:1. As a result, a total of 15 fractions were obtained and they were combined into 10 fractions through TLC and HPLC. Compound 1 (10 mg), Compound 2 (5.5 mg) and Compound 3 (15 mg) were obtained as pure single substances from the 1st fraction (255 mg) through HPLC (solvent: 40-50% ACN).

Example 3: Structural Identification of Compound 1

Compound 1 was separated as a scarlet powder. Two proton peaks at δH 5.81 (2H, s, H-4, H-6) in the $^1$H NMR spectrum were identified as aromatic protons at 1, 3 and 5 positions by $^{13}$C NMR. A butyryl group was inferred from the correlation between two methylene protons at 2.97 (2H, t, J=7.4 Hz, H-2') and 1.60 (2H, m, H-3') and a methyl proton 0.92 (3H, t, J=7.4 Hz, Me-4'). δC 205.55 (C-1'), 164.90 (C-5), 164.66 (C-1, 3), 104.26 (C-2), 95.10 (C-4, 6), 45.48 (C-2'), 18.19 (C-3') and 14.33 (C-4') were identified from $^{13}$C NMR. The backbone of phloroglucinol was identified based on the NMR result. After comparing with the reference, Compound 1 was identified as butyryiphloroglucinol.

Example 4: Structural Identification of Compound 2

Compound 2 was separated as a scarlet powder. One proton peak at δH 5.92 (s, H-6) in the $^1$H NMR spectrum was identified as aromatic protons at 1, 3 and positions by $^{13}$C NMR. A propionyl group was inferred from the correlation between a methylene proton 3.09 (2H, q, H-2') and a methyl proton (3H, t, J=7.4 Hz, Me-3') and one methyl proton 1.94 (3H, s, Me-1'') was identified. δC 208.70 (C-1'), 163.46 (C-5), 162.30 (C-3), 159.99 (C-1), 103.65 (C-4), 102.09 (C-2), 93.33 (C-6), 36.61 (C-2'), 7.93 (C-3') and 5.91 (C-1'') were identified from $^{13}$C NMR. The backbone of phloroglucinol was identified based on the NMR result. After comparing with the reference, Compound 2 was identified as 2-propionyl-4-methylphloroglucinol.

Example 5: Structural Identification of Compound 3

Compound 3 was separated as a scarlet powder.
One proton peak at δH 6.01 (s, H-6) in the $^1$H NMR spectrum was identified as aromatic protons at 1, 3 and 5 positions by $^{13}$C NMR. A butyryl group was inferred from the correlation between a methylene proton 2.97 (2H, t, J=7.4 Hz, H-2'), another methylene proton 1.60 (2H, m, H-3') and a methyl proton 0.92 (3H, t, J=7.4 Hz, Me-4') and one methyl proton 1.84 (3H, s, Me-1'') was identified. δC 206.52 (C-1'), 163.68 (C-5), 163.03 (C-3), 161.24 (C-1), 103.23 (C-4), 102.69 (C-2), 95.74 (C-6), 41.97 (C-2'), 19.44 (C-3'), 13.57 (C-4') and 7.84 (C-1'') were identified from $^{13}$C NMR. The backbone of phloroglucinol was identified based on the NMR result.
After comparing with the reference, Compound 3 was identified as 2-butyryl-4-methylphloroglucinol.

Test Example 1: Investigation of Toxicity of Identified Compounds

The cytotoxicity of Compounds 1-3 separated and identified in Examples 1-5 was investigated by MTT-based cytotoxicity assay. APP*t-CHO cells treated with Compounds 1-3 were cultured for 24 hours. After adding a 5 mg/mL MTT solution, the cells were cultured for 4 hours. After removing the culture medium and lysing the cells for 30 minutes by adding DMSO, absorbance was measured at 540 nm using the Emax precision microplate reader (Molecular Devices, CA, USA). Compounds 1 and 2 showed no toxicity even at the concentration of 100 μg/mL, whereas Compound 3 showed toxicity at the concentration of 30 μg/mL or higher (see FIGS. 12 and 13).

Test Example 2: Suppression of β-Amyloid Formation by Phloroglucinol-Based Compounds In order to evaluate the ability of suppressing β-amyloid formation of Compounds 1-3, $APP_{wt}$-CHO cells obtained by overexpressing APP in CHO cells were used and the amount of the sAPPβ protein cleaved by β-secretase and released out of the cells was measured by western blot. When the APP precursor protein is cleaved first by β-secretase, sAPPβ is released out of the cell. The protein remaining attached to the membrane is cleaved again by γ-secretase to produce β-amyloid. Accordingly, the amount of β-secretase and sAPPβ is proportional to the amount of the produced β-amyloid. Therefore, the amount of the two proteins was measured by western blot.

As a result, Compound 1 (butyrylphloroglucinol) reduced the amount of the sAPPβ protein by about 20% at the concentration of 10 μg/mL and by about 70% at the concentration of 20 μg/mL as compared to the control group. Compound 2 (2-propionyl-4-methylphloroglucinol) reduced the amount of sAPPβ by about 40% at 20 μg/mL and by about 80% at 100 μg/mL as compared to the control group. Compound 3 (2-butyryl-4-methylphloroglucinol) reduced the amount of sAPPβ by about 40% at 10 μg/mL and by about 80% at 20 μg/mL as compared to the control group. Also, Compound 1 (butyryiphloroglucinol) reduced the amount of the β-secretase protein by about 10% at 10 μg/mL and by about 30% at 20 μg/mL. Compound 2 (2-propionyl-4-methylphloroglucinol) reduced the amount of β-secretase by about 40% at 20 μg/mL and by about 60% at 100 μg/mL as compared to the control group. Compound 3 (2-butyryl-4-methylphloroglucinol) reduced the amount of β-secretase by about 20% at 10 μg/mL and by about 30% at 20 μg/mL as compared to the control group. To conclude, all of Compounds 1-3 showed the ability of suppressing the formation of the β-amyloid protein (FIGS. 14-21).

What is claimed is:

1. A pharmaceutical composition for treating Alzheimer's disease, comprising one or more phloroglucinol-based compound selected from the group consisting of butyrylphloroglucinol, 2-propionyl-4-methylphloroglucinol and 2-butyryl-4-methylphloroglucinol, an isomer thereof or a salt thereof,
wherein the pharmaceutical composition further comprises a substance effective in treating dementia.

2. The pharmaceutical composition for preventing or treating Alzheimer's disease according to claim 1, wherein the pharmaceutical composition comprises butyrylphloroglucinol as an active ingredient.

3. The pharmaceutical composition for preventing or treating Alzheimer's disease according to claim 1, wherein the pharmaceutical composition comprises butyrylphloroglucinol as a single active ingredient.

4. The pharmaceutical composition for preventing or treating Alzheimer's disease according to claim 1, wherein the pharmaceutical composition comprises 2-propionyl-4-methylphloroglucinol as an active ingredient.

5. The pharmaceutical composition for preventing or treating Alzheimer's disease according to claim 1, wherein the pharmaceutical composition comprises 2-propionyl-4-methylphloroglucinol as a single active ingredient.

6. The pharmaceutical composition for treating Alzheimer's disease according to claim 1, wherein the pharmaceutical composition comprises 2-butyryl-4-methylphloroglucinol as an active ingredient.

7. The pharmaceutical composition for treating Alzheimer's disease according to claim 1, wherein the pharmaceutical composition comprises 2-butyryl-4-methylphloroglucinol as a single active ingredient.

8. The pharmaceutical composition for treating Alzheimer's disease according to claim 1, wherein the salt is a physiologically acceptable salt of an inorganic acid, an organic acid, an inorganic base or an organic base.

9. The pharmaceutical composition for treating Alzheimer's disease according to claim 1, wherein the phloroglucinol-based compound is isolated from *Dryopteris crassirhizoma*.

10. The pharmaceutical composition for treating Alzheimer's disease according to claim 9, wherein the phloroglucinol-based compound is isolated by extracting *Dryopteris crassirhizoma* with one or more solvent selected from the group consisting of propanol, isopropanol and methanol.

11. The pharmaceutical composition for treating Alzheimer's disease according to claim 10, wherein the solvent extract is fractionated simultaneously or sequentially with one or more solvent selected from the group consisting of hexane, methylene chloride, ethyl acetate, butanol and water.

12. The pharmaceutical composition for treating Alzheimer's disease according to claim 11, wherein the fraction is separated into a single substance by being subjected to ion-exchange chromatography and then to silica gel chromatography or medium pressure liquid chromatography (MPLC).

13. The pharmaceutical composition for treating Alzheimer's disease according to claim 1, wherein the pharmaceutical composition comprises one or more selected from the group consisting of an inert carrier and a diluent.

14. The pharmaceutical composition for treating Alzheimer's disease according to claim 1, wherein the pharmaceutical composition is prepared into an oral or parenteral formulation.

15. The pharmaceutical composition for treating Alzheimer's disease according to claim 14, wherein the pharmaceutical composition is prepared into the oral or parental formulation selected from the group consisting of a tablet, a capsule, a pill, a powder, a granule, a suspension, a syrup, a cream, a lotion, an ointment, a liquid, a gel, a cataplasma, a patch, an aerosol, a fluid extract, an elixir, an infusion, a sachet and an injection.

16. The pharmaceutical composition for treating Alzheimer's disease according to claim 1, wherein the substance is selected from the group consisting of tacrine, donepezil, rivastigmine and galantamine.

17. The pharmaceutical composition for preventing or treating Alzheimer's disease according to claim 1, wherein a concentration of butyrylphloroglucinol is 10 μg/mL to 20 μg/mL, a concentration of 2-propionyl-4-methylphloroglucinol is 20 μg/mL to 100 μg/mL, and a concentration of 2-butyryl-4-methylphloroglucinol is 10 μg/mL to 20 μg/mL.

18. A method of treating Alzheimer's disease comprising administering a pharmaceutically effective amount of the pharmaceutical composition of claim 1 to a subject suffering the Alzheimer's disease.

\* \* \* \* \*